(12) United States Patent
Herweg et al.

(10) Patent No.: US 9,775,688 B2
(45) Date of Patent: Oct. 3, 2017

(54) IMPLANT ANALOG

(75) Inventors: Holger Herweg, Basel (CH); Reto Mettler, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 13/116,229

(22) Filed: May 26, 2011

(65) Prior Publication Data

US 2011/0294093 A1    Dec. 1, 2011

(30) Foreign Application Priority Data

May 26, 2010  (DE) .......................... 10 2010 021 601

(51) Int. Cl.
*A61C 8/00* (2006.01)
(52) U.S. Cl.
CPC .................. *A61C 8/0001* (2013.01)
(58) Field of Classification Search
CPC ............. A61C 2008/0084; A61C 8/00–8/0098
USPC .......................... 433/72–76, 201.1, 172–176
See application file for complete search history.

(56) References Cited

U.S. PATENT DOCUMENTS

| | | | | |
|---|---|---|---|---|
| 5,316,476 A | * | 5/1994 | Krauser ....................... | 433/173 |
| 5,658,147 A | * | 8/1997 | Phimmasone ......... | A61C 9/002 |
| | | | | 433/173 |
| 5,873,721 A | * | 2/1999 | Willoughby .................. | 433/173 |
| 6,099,312 A | * | 8/2000 | Alvaro ......................... | 433/174 |
| 2003/0162148 A1 | * | 8/2003 | Prestipino ............ | A61C 8/0001 |
| | | | | 433/173 |
| 2006/0228672 A1 | * | 10/2006 | Hurson ........................ | 433/173 |
| 2007/0224576 A1 | * | 9/2007 | Ihde et al. .................... | 433/173 |
| 2008/0064010 A1 | * | 3/2008 | Ten Bruggenkate ......... | 433/174 |
| 2008/0241789 A1 | * | 10/2008 | Mundorf ....................... | 433/173 |
| 2009/0081613 A1 | * | 3/2009 | Ihde et al. .................... | 433/173 |
| 2009/0305190 A1 | | 12/2009 | Zipprich | |

FOREIGN PATENT DOCUMENTS

DE    10 2006 018 726 A1    10/2007

* cited by examiner

*Primary Examiner* — Yogesh Patel
(74) *Attorney, Agent, or Firm* — Scully, Scott, Murphy & Presser, P.C.

(57) ABSTRACT

The present invention refers to an analog implant for a dental model which has such a geometry as to allow its height positioning, axial positioning and angular orientation in a bore or blind hole of a dental model, the analog implant having a distal portion and a proximal portion, where the proximal portion has a rotationally symmetric geometry in a cross-section which is perpendicular to the axis of the proximal portion, where the rotationally symmetric geometry is adapted to ensure securing against rotation and repositioning of the analog implant in a bore or blind hole of a dental model, the external geometry of the proximal portion being such that the analog implant can be removed from the dental model, and where a proximally positioned shoulder of the distal portion forms a height stop which allows precise height positioning of the analog implant on the dental model or on the soft tissue of the dental model, respectively.

15 Claims, 8 Drawing Sheets

IMPLANT ANALOG

The present invention refers to an analog implant, in particular an analog implant which can be inserted in a CAD/CAM-produced dental model for adaptation of a dental prosthesis.

STATE OF THE ART

From US 2003/0 162 148 A1, an analog implant for the adaptation of dental prostheses is known which can be embedded in a plaster model. Normally, for adaptation of a dental prosthesis after the healing phase of a dental implant screw implanted in a bone tissue, a plaster model is produced which reproduces the dental position of the patient's mouth with the implant screw. Subsequently, the analog implant is inserted in a bore hole suitably formed in the plaster model, subsequent to which the technician can adjust the dental prosthesis. The analog implant known from US 2003/0 162 148 A1 is disadvantageous insofar as it contains no information which would make it possible to insert the analog implant in a CAD/CAM-produced dental model.

Generally, the prior art suffers a problem insofar as it is presently only possible to produce a dental model with an analog implant by casting the jaw of the patient with a corresponding casting material and by embedding a casting post in the casting material. The casting post is indispensable for correctly positioning the analog implant in the dental model. It is presently not possible, however, to produce a dental model with an analog implant from scanned intraoral data by CAM/CAD methods.

SUMMARY OF THE INVENTION

Therefore, it is an object of the present invention to provide an analog implant which overcomes the drawbacks mentioned above and is particularly suitable for adapting a dental prosthesis to a CAD/CAM dental model outside the mouth of the patient.

This object is achieved according to claim 1. Advantageous further developments of the invention are disclosed in the dependent claims.

BRIEF DESCRIPTION OF THE DRAWINGS

A detailed description of the invention follows with reference to preferred, non-limiting embodiments of the invention and to the accompanying drawings wherein.

DESCRIPTION OF PREFERRED EMBODIMENTS OF THE INVENTIONS

In the present description, the term "distal" designates an area further away from the dental model and the term "proximal" designates an area closer to the dental model. Within the framework of the description, "distal" is synonymous with "coronal" and "proximal" with "apical".

Figure 1:
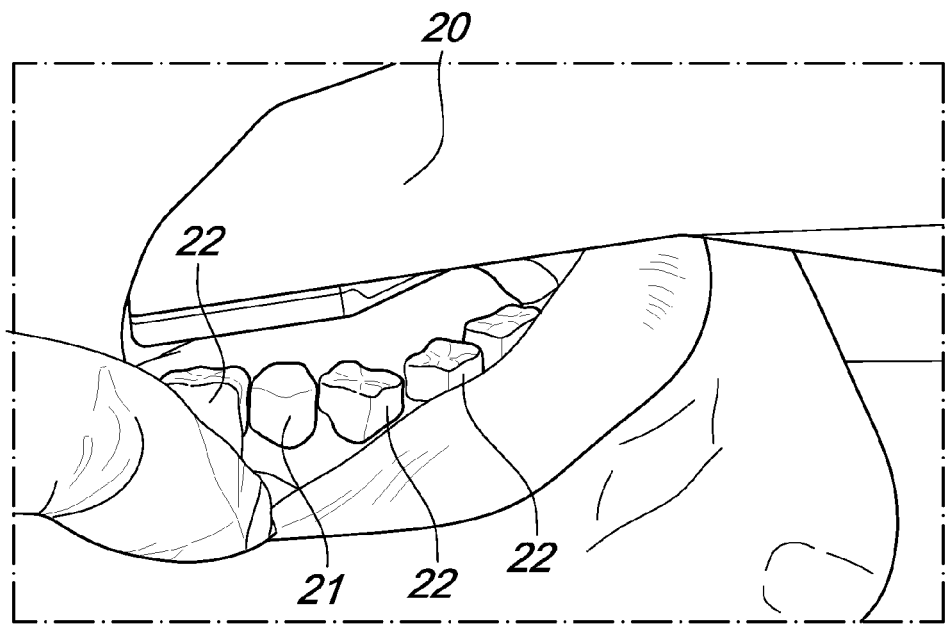
FIG. 1 is a representation of the mouth of a patient with a scan body which is inserted on an osteointegrated dental implant screw.

With reference to FIG. 1, there is shown the open mouth of a patient after the osteointegration of a dental implant screw with a connected scan body 21. The scan body 21 comprises a proximal end which fits precisely into the distal end of the dental implant screw. In addition, the scan body 21 comprises a distal end with a defined surface which can be scanned, which is preferably polygonal and which extends from the soft tissue so as to be detected by a scanner 20. The position and direction of the dental implant screw can be determined precisely from the scanned data of the position and direction of the distal part of the scan body 21, in a manner known to the person skilled in the art which is not to be further explained here. During the scanning process, the scanner 20 is located in the mouth of the patient and directed mainly on the scan body 21; however, it can also scan the areas adjacent to the scan body 21 so that the intact neighboring teeth 22 are scanned as well. The position and direction of the scan body 21 are detected in relation to the intact neighboring teeth 22 as a digital virtual impression of this part of the mouth. Thus, there is a certain analogy to a conventional casting process wherein a plaster model of the dental area to be restored and its intact surroundings is produced. It is also conceivable to move the scanner 20 over a larger area of the mouth to scan the entire lower and upper jaws of the patient and thus obtain a complete picture of the mouth of the patient. It is also possible to use the scanner 20 to scan individual portions of the mouth of the patient and assemble them by known methods. Thus, with the recorded virtual impression data, a digital dental model can be produced by means of which at a later point in time the CAM/CAD dental model 10 can be produced, for instance, by milling.

Figure 2:
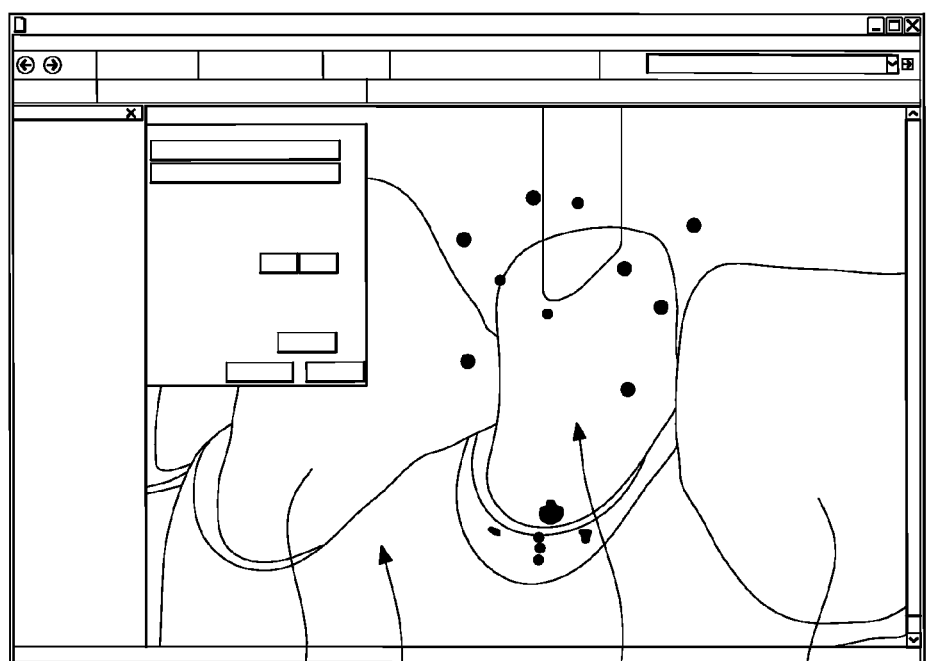
FIG. 2 is a monitoring screen copy of a CAD system showing the impression of the mouth of the patient in a specific state during design of a dental prosthesis.

FIG. 2 shows a screen copy of a CAD software for designing a dental prosthesis 7. Preferably, a virtual impression is represented first which shows the scanned portion of the mouth of the patient in accordance with the virtual impression data, with the neighboring intact teeth 12 as impressions of the original neighboring intact teeth 22, with the soft tissue 11 and with a calculated bore or blind hole of the distal end of the dental implant screw which is calculated using the known geometry of the scan body 21. Based on the virtual impression data, a prosthesis structure having an abutment 6 and a dental prosthesis 7 can be designed.

Figure 3:
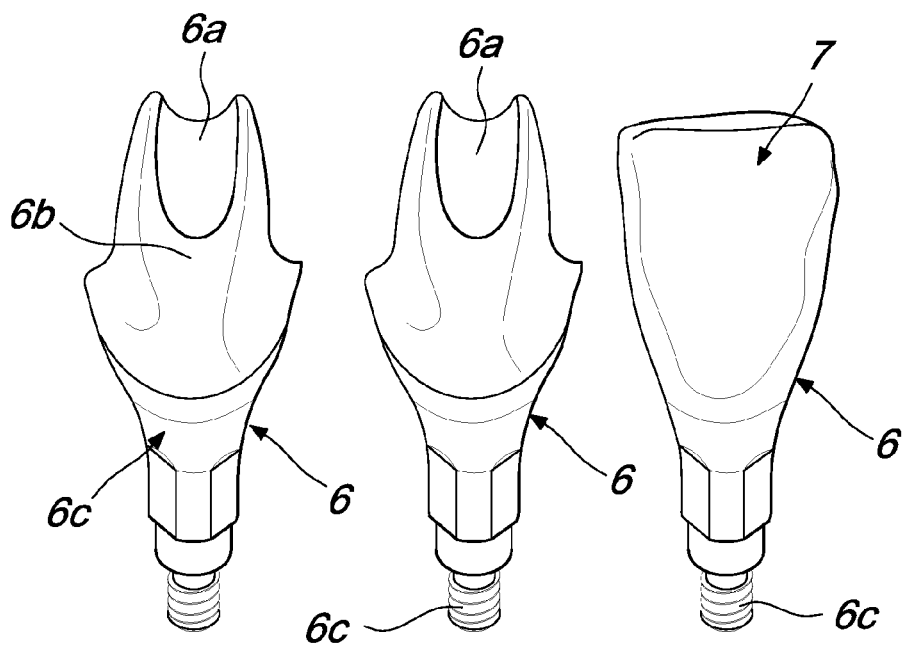
FIG. 3 is a three-dimensional lateral view of two abutments made of different materials and one abutment with the dental prosthesis placed on top of it.

The abutment 6 can either be selected from a series of finished abutments or manufactured as a single piece (customized abutment). FIG. 3 shows, in the center and on the left, two abutments 6 manufactured from different materials (ceramics and titanium, respectively) which comprise a proximal end 6c that can be connected to the distal end of the dental implant screw. A connecting screw shown at the proximal end 6c of the abutment 6 can be inserted into the abutment through a distal opening 6a at the distal end 6b of the abutment. Furthermore, FIG. 3 shows, on the right, an abutment 6 connected to the dental prosthesis 7.

Figure 4:
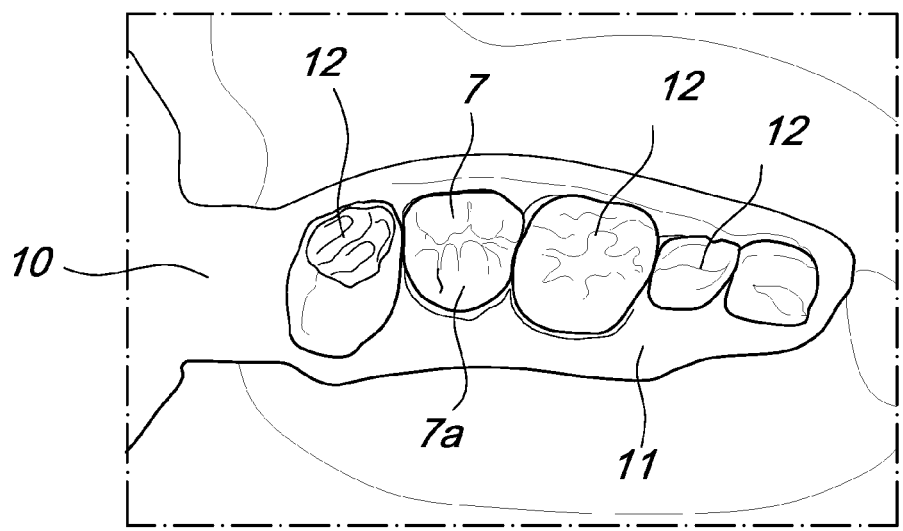
FIG. 4 is a top view of a dental model with a dental prosthesis placed on top of it.

FIG. 4 shows a portion of a dental model 10 produced with CAM/CAD methods, which model was produced using the virtual impression data, where the dental model 10 includes a plurality of imprints of intact teeth. In the top view of FIG. 4, the dental prosthesis 7 with a respective masticatory surface 7a can also be seen. The reference number 11 designates the position of the soft tissue in the dental model 10.

Figure 5:
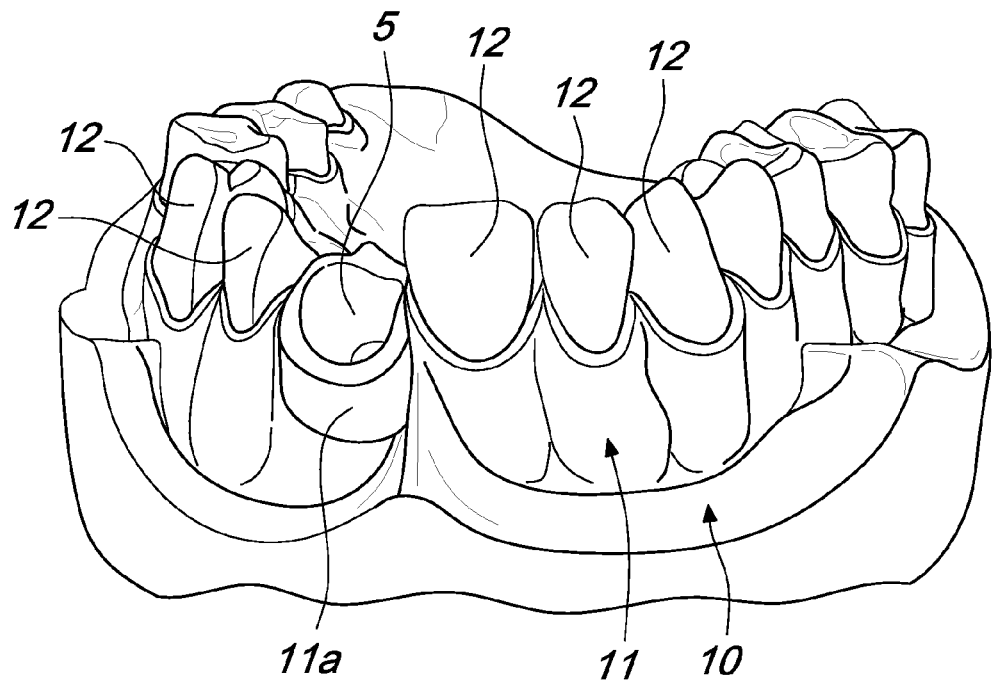
FIG. 5 is a three-dimensional view of a dental model with an inserted soft-tissue model around a bore hole in which an analog implant can be inserted.

FIG. 5 shows the complete dental model 4 wherein the same reference numbers are used as in FIG. 4. As shown in FIG. 5, the soft tissue 11 is milled partly integral with the dental model 10 (or manufactured with equivalent procedures). A part 11a of the soft tissue 11, however, can also be processed separately for easier manufacturing. In addition, by separate processing of the part 11a of the soft tissue 11, the precision at a connecting interface 5 of the subsequently described analog implant 1 with an abutment can be increased.

Figure 6:
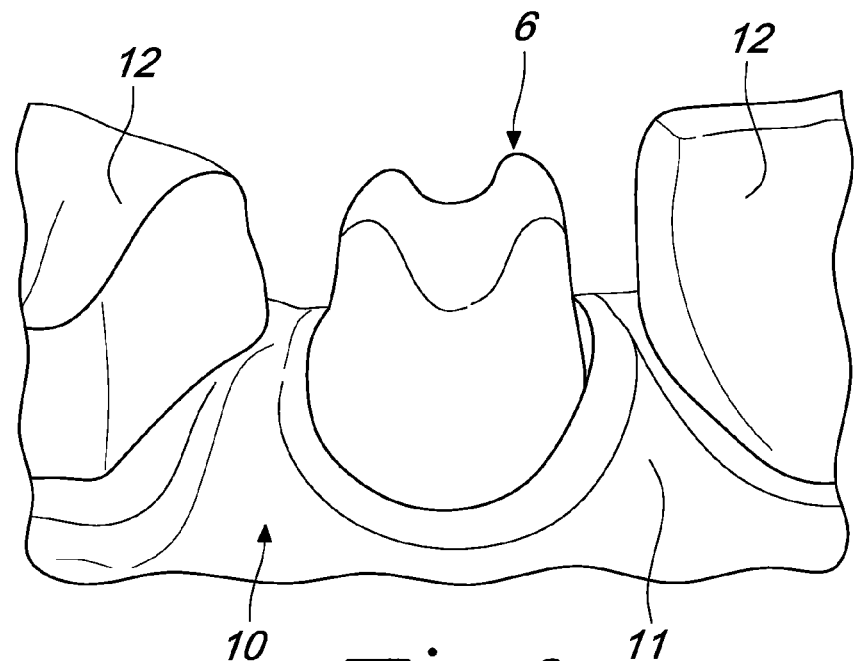
FIG. 6 is a three-dimensional view of a part of the dental model with an abutment placed on top of the not visible analog implant which protrudes out of the soft tissue and on top of which the dental prosthesis is to be placed.

FIG. 6 shows an enlarged portion of the dental model 10 with the intact teeth 12, the soft tissue 11 and the abutment 6 placed on the analog implant (not shown), where in this embodiment the soft tissue 11 of the dental model is formed in an integral manner.

Figure 7:
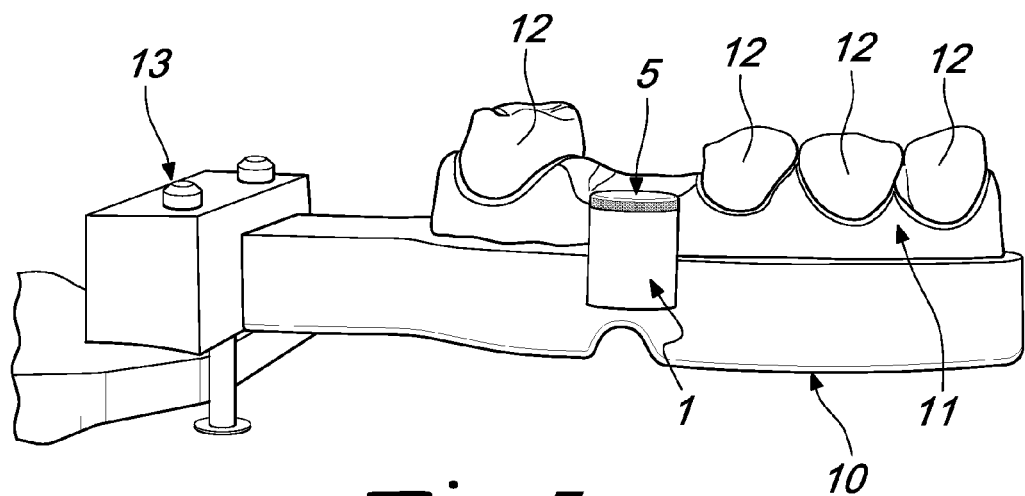
FIG. 7 is a three-dimensional lateral view of a dental model milled with CAM/CAD methods or processed otherwise, which shows a section around the analog implant in a cross-sectional view.

With reference to FIG. 7, a three-dimensional lateral view of the dental model 10 milled with CAM/CAD methods or processed otherwise is indicated, which shows a cross-sectional view (corresponding approximately to the portion in FIG. 4) around the analog implant 5. The dental model 10 in the shown figure is connected to a milling unit by means of a connecting device 13.

Figures 8A, 8B:
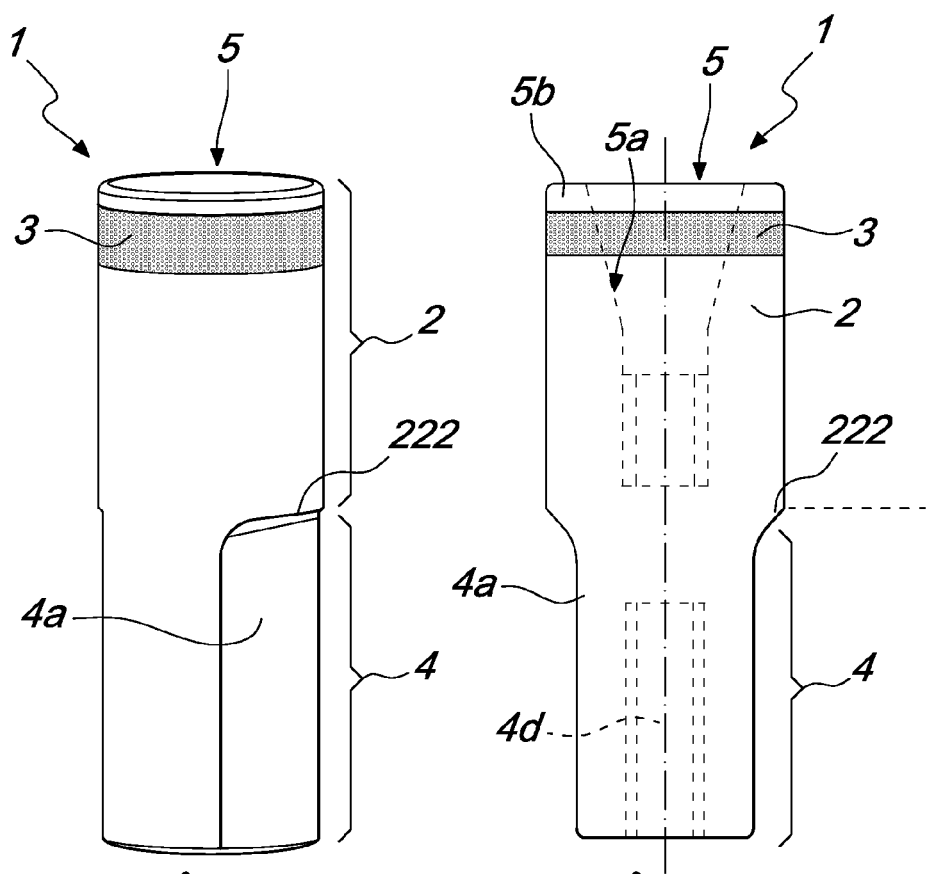
FIG. 8*a* is a three-dimensional lateral view of an analog implant.
FIG. 8*b* is a lateral view of the analog implant of FIG. 8*a* in a position slightly rotated axially.

As can be seen in FIGS. 7, 8a and 8b, the analog implant 1 according to the invention has a specific asymmetrical geometry which determines its precise height position, axial position and angular orientation in the bore or blind hole of the dental model. The bore or blind hole calculated using the known geometry of the scan body 21 precisely reflects the height position, the axial position and the angular orientation of the dental implant screw so that the analog implant 1 according to the invention also precisely follows the orientation of the dental implant screw, thus allowing a precise adjustment of the dental prosthesis 7 on the dental model.

The analog implant 1 preferably has, as shown in FIGS. 8a and 8b, a substantially cylindrical distal portion 2 comprising the connecting interface 5 with the abutment 6, which is substantially identical with the connecting interface of a dental implant screw. In addition, the analog implant 1 can be provided at its connecting interface 5 with a recess or a blind hole 5a and a surface 5b so as to facilitate placement of the abutment 6. A circumferential recess 3 can be provided as a further positioning aid an/or for better connection to the abutment 6. A proximally positioned shoulder 222 of the distal portion 2 provides a height stop which allows the precise positioning of the analog implant 1 in the height on the dental model 10 or the soft tissue 11 of the dental model 10.

The proximal portion 4 of the analog implant 1 is non-circular symmetric and adapted for securing the analog implant 1 in the bore of the dental model 10 in a specific angular position. Furthermore, a threaded bore 4d can be provided on the analog implant 1 for securing to the dental model. According to the invention, the proximal portion 4 is formed with at least two flattened areas 4a which are obtained by the removal of corresponding portions of a cylinder and which are formed rotationally symmetrically around the axis of the proximal, non-circular symmetric portion 4, enabling the axial securing of the analog implant 1 and its repositioning in a correspondingly formed bore or blind hole of the dental model 10. Due to the geometry of the analog implant 1 of the embodiment in FIG. 8a or 8b, respectively, the particular advantage consists in the fact that the analog implant is removable from the dental model 10 and able to be repositioned in two positions. In addition, it is possible to shorten the analog implant 1 at the proximal, non-circular symmetric portion 4 so that the analog implant 1 can be adjusted in length according to the dimensions of the dental model 10. According to the invention, it is conceivable to increase the number of flattened portions 4a while maintaining the rotational symmetry about the axis of the proximal, non-circular symmetric portion 4 in order to increase the number of positions of the analog implant 1 in the dental model 10 accordingly. Obviously, in this case, the shape of the bore or of the blind hole, respectively, of the dental model 10 must be adapted to the increased number of flattened rotationally symmetric portions 4a. The external geometry of the proximal portion 4 is such that the analog implant 1 can be removed from the dental model 10.

Figure 8C:
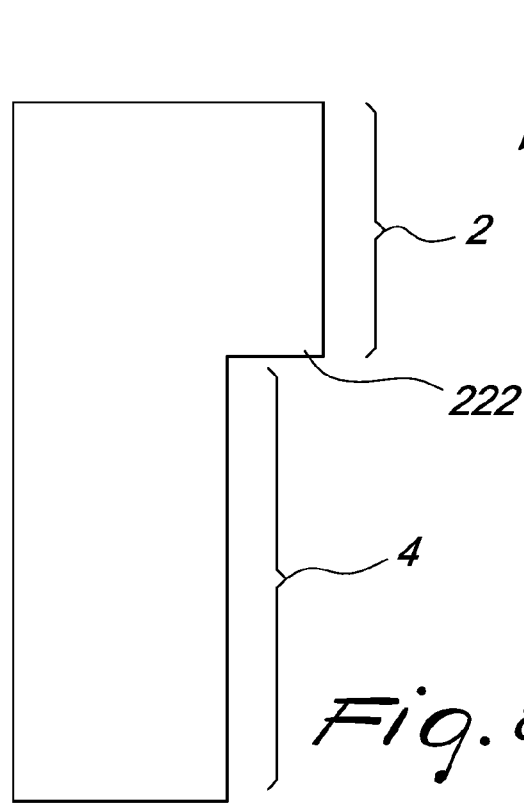
FIG. 8*c* is a schematic view of an analog implant modified with reference to FIG. 8*b*.
Figure 8D:
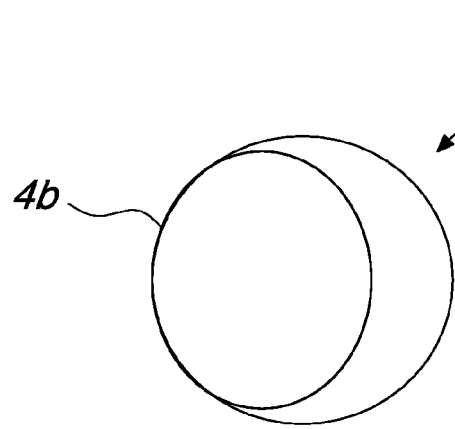
FIG. 8*d* is a view from below of FIG. 8*c*.

In the embodiment in FIGS. 8c and 8d, the proximal portion 4 is provided with an elliptical cross-section 4b according to the invention. The distal portion 2 corresponds to that of the embodiment in FIGS. 8a and 8b and will therefore not be explained in detail. The embodiment in FIGS. 8c and 8d offers the same advantages as the one in FIGS. 8a and 8b since its geometry allows a removal and an axial adaptation of the length of the analog implant 1 as well. In addition, the analog implant 1 of the embodiment in FIGS. 8c and 8d (like the one in FIGS. 8a and 8b) can be repositioned by a dental technician in two positions within the bore or blind hole of the dental model 10, where also in the case of the embodiment in FIGS. 8c and 8d, the bore or blind hole of the dental model 10 has a shape complementary to the elliptical shape of the portion 4. Also in this embodiment, the external geometry of the proximal portion 4 is such that the analog implant 1 can be taken out of the dental model 10.

Figure 9A:
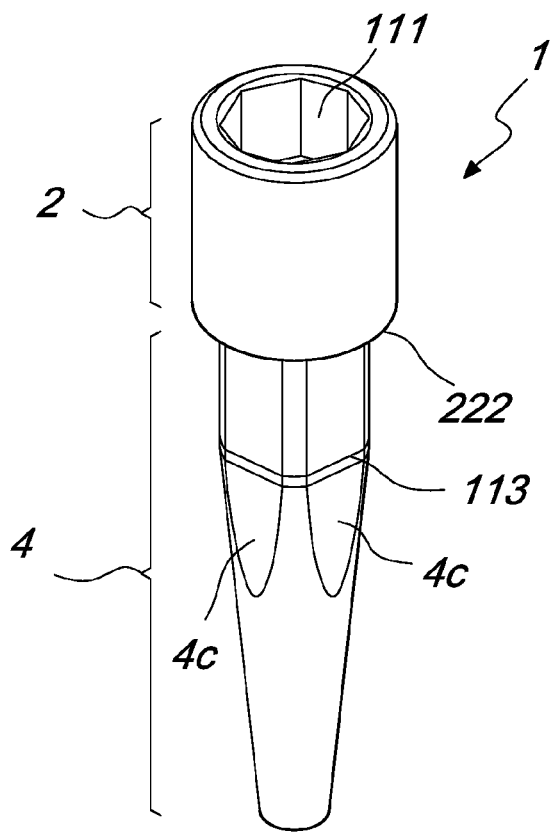
FIG. 9*a* is a perspective view of another embodiment of an analog implant.

FIG. 9a shows another embodiment of an analog implant 1 having a first distal portion 2 and a second proximal portion 4. The first distal portion 2 is preferably circular symmetric and contains, as usual, a blind hole or opening which is only partly visible in the perspective view and can be equipped with a suitable connection profile 111 for receiving an assembly portion or abutment (not shown), secured against rotation. The second proximal portion 4 is equipped with a first, preferably cylindrical, distal portion and a second, preferably conical, proximal portion. According to the invention, however, it is also conceivable to embody the second proximal portion 4 cylindrical or conical in its entirety. In any case, according to the invention, the second proximal portion 4 is formed with a plurality of flattened areas or recesses 4c, which allow its positioning secure against rotation and the repositioning in a dental model not shown in FIG. 9a and which are arranged rotationally symmetrically around the axis of the second proximal portion 4. Preferably, the flattened areas or recesses 4c are four in number and their arrangement around the axis of the second portion 4 is rotationally symmetrical. The number of flattened areas or recesses 4c, however, can also be any other number larger than two, while maintaining the rotational symmetry. The proximally positioned shoulder 222 of the first distal portion 2 of the analog implant 1 provides a height stop which allows a precise height positioning of the analog implant 1 on the dental model 10 or the soft tissue 11 of the dental model 10. The embodiment in FIG. 9a offers the same advantages as the one in FIGS. 8c and 8d since its geometry allows a removal, a repositioning and an axial adaptation of the length of the analog implant 1 as well. In addition, the ability to be repositioned is adapted with the number of flattened portions or recesses 4c. Obviously, in this case, the shape of the bore or of the blind hole, respectively, of the dental model 10 must be adapted to the increased number of flattened rotationally symmetric portions 4a. The external geometry of the proximal portion 4 is such that the analog implant 1 can be removed from the dental model 10 in this embodiment as well.

FIG. 9a shows an exemplary embodiment of the connection profile 111 which is formed inside the blind hole in the cylindrical distal portion 2 of the analog implant. Preferably, the connection profile 111 is octagonal, where the octagon can assume, in addition to the shape represented in FIG. 9a, also the shape of the synOcta® connection of the owner of the present application (see FIGS. 10a through 10d). The external geometry of the analog implant 1 with the flattened areas or recesses 4c is compatible with the connection profile. Preferably, the relationship of the connection profile 111 with the flattened areas or recesses 4c is predefined. The cylindrical distal portion 2 can have different dimensions, such as e.g. NN ("Narrow Neck"), RN ("Regular Neck"), WN ("Wide Neck"), RC ("Regular CrossFit™"), NC ("Narrow CrossFit™") and the like which are manufactured and distributed by the owner of the present application.

Figure 9B:
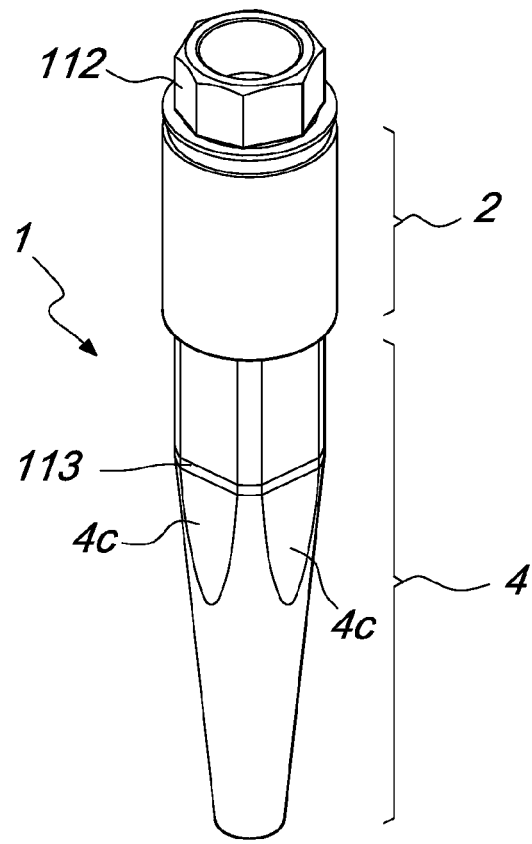
FIG. 9*b* is a perspective view of a first modification of the analog implant in FIG. 9*a*.
Figure 10A:
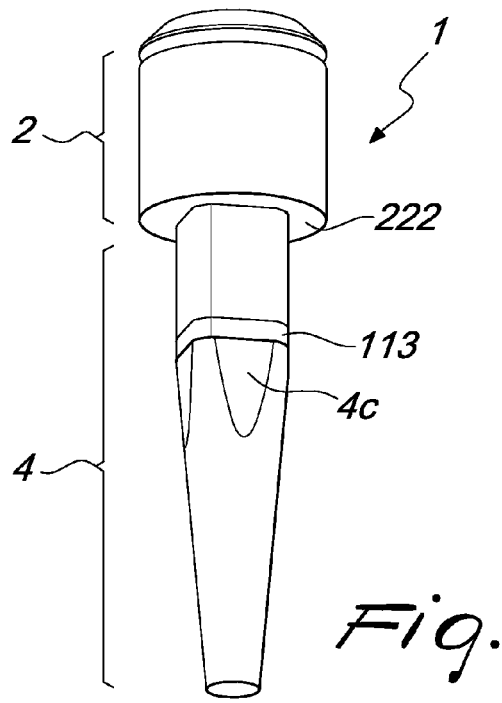
FIG. 10*a* is a perspective view of a second modification of the analog implant in FIG. 9*a*.
Figure 10B:
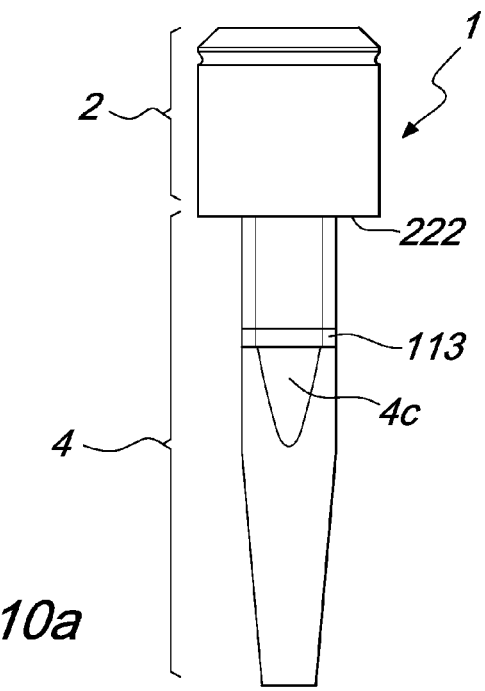
FIG. 10*b* is a lateral view of the second modification of FIG. 10*a*.
Figure 10C:
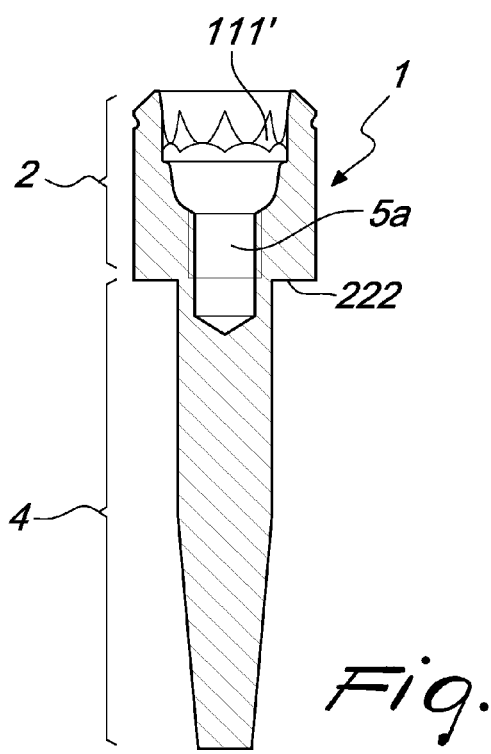
FIG. 10*c* is a sectional view of the second modification of FIG. 10*a*.
Figure 10D:
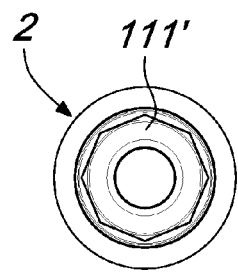
FIG. 10*d* is a top view of the second modification of FIG. 10*a*.
Figure 11A:
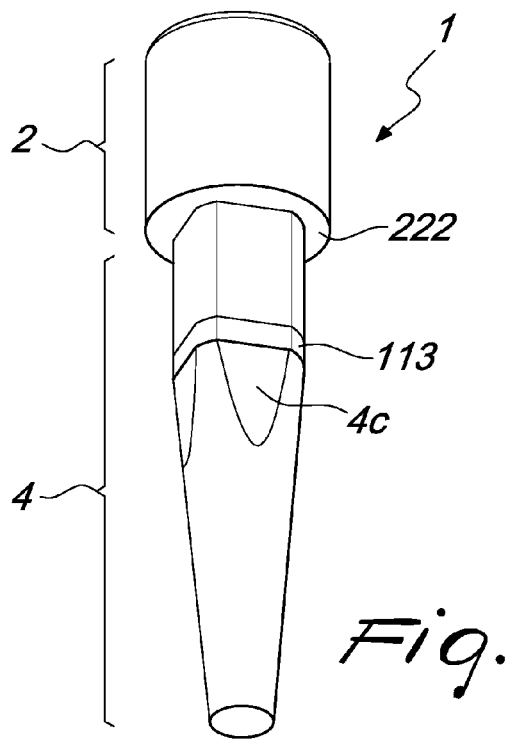
FIG. 11*a* is a perspective view of a third modification of the analog implant of FIG. 9*a*.
Figure 11B:
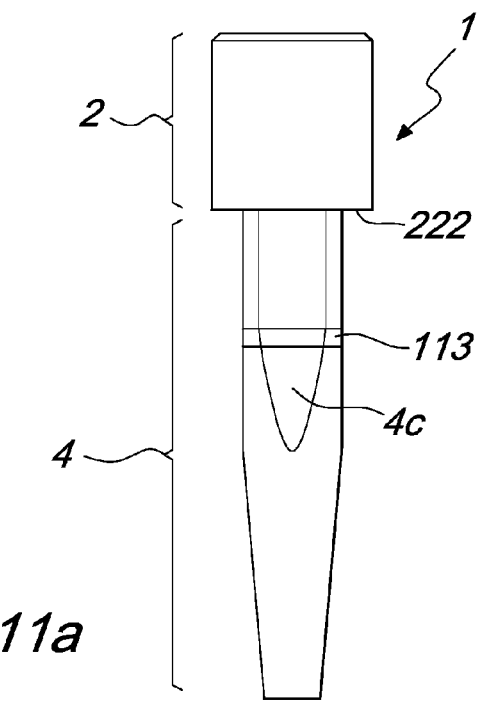
FIG. 11*b* is a lateral view of the third modification of FIG. 11*a*.
Figure 11C:
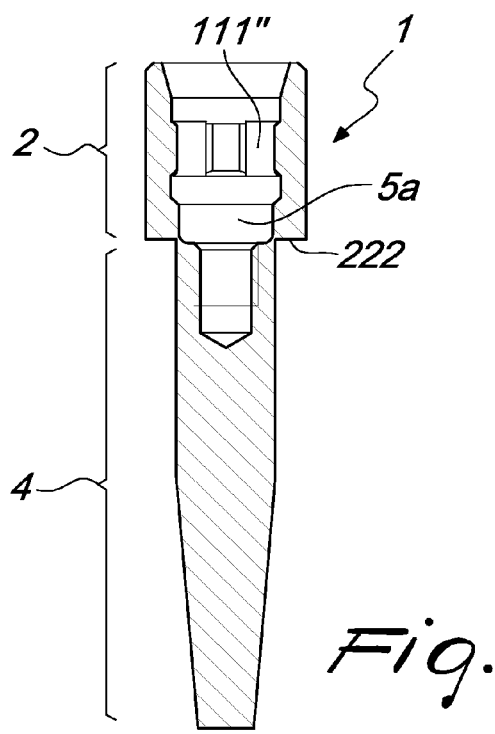
FIG. 11*c* is a sectional view of the third modification of FIG. 11*a*.
Figure 11D:
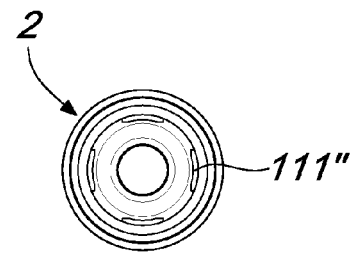
FIG. 11*d* is a top view of the third modification of FIG. 11*a*.

In the first modification of FIG. 9b, the connection profile 112 is formed as a polygon above the cylindrical distal portion 2. Preferably, the polygon is an octagon. This modification does basically not differ from the embodiment in FIG. 9a in other regards. In particular, advantageously, the relationship of the connection profile 112 with the flattened areas or recesses 4c is predefined in the first modification of FIG. 9b as well.

In the second modification of FIGS. 10a through 10d, the connection profile 111' is formed as a synOcta® connection in the cylindrical distal portion 2 of the analog implant 1. In addition, the blind hole 5a of the analog implant 1 is visible in its full length in the cross-sectional view of FIG. 10c. This second modification does basically not differ from the embodiment in FIG. 9a in other regards, and therefore the individual components of this modification are not explained in detail. In particular, advantageously, the relationship of the connection profile 111' with the flattened areas or recesses 4c is predefined in the second modification of FIGS. 10a through 10d as well.

In the third modification of FIGS. 11a through 11d, the connection profile 111" is formed as a CrossFit™ connection of the owner of the present application with self-locating internal prosthetic connecting elements in the cylindrical distal portion 2 of the analog implant 1. In addition, the blind hole 5a of the analog implant 1 is visible in its full length in the cross-sectional view of FIG. 11c. This third modification does basically not differ from the embodiment in FIG. 9a in other regards, and therefore the individual components of this modification are not explained in detail. In particular, advantageously, the relationship of the connection profile 111" with the flattened areas or recesses 4c is predefined in the third modification of FIGS. 11a through 11d as well.

All described embodiments of the analog implant 1 according to the invention advantageously comprise a marking on the proximal, non-circular symmetric portion 4 which shows the dental technician up to which point the analog implant 1 can be shortened without losing its functionality. In other words, the marking shows the maximum length by which the analog implant 1 can be shortened without its inner blind hole being damaged and/or its securing against rotation on the dental model 10 being impaired. Thus, the analog implant 1 can be adjusted in length according to the dimensions of the dental model 10 and its functionality is not impaired. This marking is designated with the reference number 113 in FIGS. 9a, 9b, 10a, 10b, 11a and 11b and can preferably consist in a laser marking.

The possibility of precise positioning of the analog implant according to the invention and the possibility of repositioning it are particularly advantageous if the analog implant is inserted in a dental model produced by means of CAM/CAD, where the dental model is produced using a digital virtual impression of the mouth or part of the mouth. In addition, the adaptability in length of the analog implant according to the invention allows its optimum integration in a dental model.

What is claimed is:

1. An analog implant for a dental model, the analog implant having a geometry to allow height positioning, axial positioning and angular orientation of the analog implant in a bore or a blind hole of the dental model,
   the analog implant having a distal portion and a proximal portion,
   the proximal portion having a rotationally symmetric geometry in a cross-section perpendicular to an axis of the proximal portion, the proximal portion having a proximal end and a distal end,
   the rotationally symmetric geometry being formed, to ensure security against rotation and to allow repositioning of the analog implant in the bore or blind hole of the dental model,
   wherein an external geometry of the proximal portion is such that the analog implant can be removed from the dental model, and
   wherein the distal portion comprises a proximal-most shoulder, wherein the proximal-most shoulder has a planar surface extending radially from the proximal portion, wherein the planar surface forms a height stop that allows precise height positioning of the analog implant on the dental model or on the soft tissue of the dental model, respectively, and wherein the proximal-most shoulder extends around the circumference of the distal portion, wherein the proximal portion comprises at least two flattened areas or recesses each starting from the planar surface of the proximal-most shoulder of the distal portion, wherein each of the flattened areas or recesses defines an axially extending surface that is planar, wherein the proximal portion further comprises axially linear areas adjacent to the flattened areas or recesses, wherein the largest transverse width of the proximal end of the proximal portion is equal to or smaller than the largest transverse width of the distal end of the proximal portion.

2. The analog implant for a dental model according to claim 1, wherein the distal portion is circular symmetric.

3. The analog implant for a dental model according to claim 2, wherein the distal and the proximal portions are not coaxial.

4. The analog implant for a dental model according to claim 1, wherein the proximal portion comprises four flattened areas or recesses which are arranged rotationally symmetrically around the axis of the proximal portion.

5. The analog implant for a dental model according to claim 4, wherein the distal portion of the analog implant contains a blind hole or opening provided with a suitable connection profile for receiving an assembly portion, secured against rotation, wherein the relationship of the connection profile with the flattened areas or recesses is predefined.

6. The analog implant for a dental model according to claim 1, wherein the distal portion of the analog implant contains a blind hole or opening provided with a suitable connection profile for receiving an assembly portion, secured against rotation, wherein the relationship of the connection profile with the flattened areas or recesses is predefined.

7. The analog implant for a dental model according to claim 6, wherein the connection profile is a polygon shape.

8. The analog implant for a dental model according to claim 7, wherein the connection profile is octagonal.

9. The analog implant for a dental model according to claim 6, wherein the connection profile is a self-locating internal prosthetic.

10. The analog implant for a dental model according to claim 1, wherein the proximal portion of the analog implant comprises a marking which indicates up to what point the analog implant can be shortened without losing functionality of the analog implant.

11. The analog implant for a dental model according to claim 10, wherein the marking is a laser marking.

12. A combination of an analog implant according to claim 1 and a dental model, wherein the dental model has a bore or blind hole formed complementary to the proximal portion of the analog implant.

13. The combination according to claim 12, wherein the dental model is produced by means of CAM/CAD.

14. The combination according to claim 13, wherein the dental model is produced by using a digital virtual impression of the mouth or part of the mouth.

15. The analog implant for a dental model according to claim 1, wherein the proximal portion has a distal cylindrical portion and a proximal conical portion.

* * * * *